United States Patent [19]

Martin

[11] Patent Number: 4,489,718
[45] Date of Patent: Dec. 25, 1984

[54] KNEE BRACE HINGE
[75] Inventor: Kelsey Martin, Azle, Tex.
[73] Assignee: Medical Designs, Inc., Azle, Tex.
[21] Appl. No.: 473,229
[22] Filed: Mar. 8, 1983
[51] Int. Cl.³ .............................................. A61F 3/00
[52] U.S. Cl. .................................... 128/80 C; 128/88
[58] Field of Search ................ 128/80 R, 80 C, 80 F, 128/88, 87 R; 3/22, 25, 26, 28, 29, 27; 403/111–113, 117

[56] References Cited
U.S. PATENT DOCUMENTS

| | | | |
|---|---|---|---|
| 3,826,251 | 7/1974 | Ross | 128/80 F |
| 4,252,111 | 2/1981 | Chao et al. | 128/80 F |
| 4,353,361 | 10/1982 | Foster | 128/80 C |
| 4,361,142 | 11/1982 | Lewis et al. | 128/80 C |

Primary Examiner—John D. Yasko
Attorney, Agent, or Firm—Wofford, Fails & Zobal

[57] ABSTRACT

An improved knee brace hinge, per se, and as a part of external bracing apparatus for controlling the degree of motion permitted by a wearer's knee and including first and second pairs of elongate relatively stiff braces that resist torsion and bending loads and adapted to lie on opposite sides of the wearer's thigh and calf; harness, with or without flexible sheets, for adjustably placing and holding the respective pairs of elongate braces in a desired obtained position on respective opposite sides of the thigh and calf of the wearer with a hinge positioned correctly adjacent the wearer's knee. The improved hinge is connected with the central ends of the respective braces on each side of the wearer's knee and each hinge employs a single cam-slot operator for simulating flexural motion of a wearer's knee and a positive lock for limiting the range of the flexural motion. The hinge has a shaft contained in a mating aperture and slidably contained within a slot for allowing the flexural motion simulating that of the wearer's knee. Specific preferred structural embodiments of the improved knee brace hinge are disclosed, including flexible plungers for limiting the movement of the cam in the slot together with indicators and respective indices for accurately presetting the movement desired to be allowed.

17 Claims, 6 Drawing Figures

KNEE BRACE HINGE

FIELD OF THE INVENTION

This invention relates to knee brace hinges. More particularly, it relates to an improved knee brace hinge for controlling the degree of motion which is permitted between the proximal and distal members of a wearer's lower limbs and including a hinge adjacent the knee, the hinge being adjustable to selectively control the amount of motion which is permitted between the proximal and distal members of the wearer's lower limbs.

DESCRIPTION OF THE PRIOR ART

A wide variety of approaches have been employed in apparatus for controlling the degree of movement of the knee of a wearer or the like. These have ranged from so called knee imobilizers such as casts or the like for rendering imobile the knee so that injured tissue might heal, support the wearer's weight or the like; through braces and the like for long term wear by a person, rather than short term rehabilitation, or allowing healing; through knee braces or supports. A very germain invention was described and claimed in a copending application Ser. No. 227,381 entitled "Brace for Articulated Limbs", Bledsoe, filed Jan. 22, 1981, assigned to the Assignee of this invention; and the contents of that application are incorporated herein by reference for details that are omitted herefrom. A good review of some prior art as shown in U.S. patents and in general employed in the past was contained therein. A portion of that material will be repeated herein to give the reader an understanding without requiring reference to another instrument. Doctors and other health technicians frequently impose restraints on a person's bones, joints and connective tissue to allow natural healing process to be started or completed before restraints are released. Also, frequently the restraints will be broadened to allow additional movement and alleviate problems with atrophying of muscles or the like. This has been a severe problem with the large leg muscles that have been imprisoned in an immobile cast for long periods of time in the past and the new theory of treatment is to allow as much excerise as possible for the patient's muscles. Moreover, the new thinking is to eliminate as much as possible the bulky conventional casts of the prior art and wear temporary apparatus that can be removed to prevent skin maceration or other complications and to accommodate changes as the healing of the injury allows such changes.

Typical of the prior art devices that have been proposed to allow accomplishing some of the foregoing advantages are those shown in the following U.S. patents. Excluded from this list of pertinent prior art are those patents which do not have a hinge and serve as "immobilizers". Also, the following group of patents are directed at apparatus, or braces that are relatively permanent for long term wear: U.S. Pat. Nos. 2,632,440; 2,943,622; 3,826,251; 3,827,431; and 3,844,279. These long term braces do not have cushion material adapted to be snugly wrapped around the wearer's leg and do not have the plurality of straps with elongated braces having a central hinge adapted to be disposed on opposite sides of the knee of the wearer and having the same structure with the same objectives as applicant's invention. Typical of the apparatus that employs a hinge with knee braces are those shown in the following U.S. Pat. No. 3,575,166 describes apparatus in which two rigid cuffs partially encircle a person's thigh and calf, respectively, encompassing about 270° of the wearer's leg member and employing a flexible elastomeric material to fill in the remaining 90° gap. A single hinge is rigidly connected at one side of the thigh and calf cuffs in order to provide at least some control with regard to the person's knee movements. U.S. Pat. No. 3,581,741 discloses similar "body" portions 18,28 which are described as being of tough, polymeric, plastic material which may be internally reinforced with glass fibers or the like. While such rigid "body portions" may be advantageous in some cases, they do not provide the flexibility that is inherent in this invention. In that patent, the inventor attempted to compensate for the necessity for having a number of different sizes by providing an inflatable bladder between the person's leg members and the rigid shells and did not have the improved hinge of this invention. U.S. Pat. No. 3,669,105 discloses a construction which has at least been manufactured and sold. It is commonly referred to as the "Lennox Hill" brace and is the type that has been worn with athletes having weakened knees. In a structural sense, the invention of this patent should be labeled a de-rotation brace that has no elongated side members, no sheet type cushions that are intended to be wrapped around a person's legs and no straps and improved hinge in accordance with this invention. U.S. Pat. No. 3,785,372 describes a rather complicated hinge appliance that is adapted to be attached to a person's leg through upper and lower casts. There is no disclosed technique for temporarily removing the Craig applicance for medical or personal reasons such as washing. U.S. Pat. No. 3,786,804 describes an apparatus having a single piece cylindrical sleeve of elastic material that is described as being dimensioned to accommodate the wearer's knee. However, it is not apparent how a single cylindrical sleeve could be ideally suited for use with a large grown man or woman or a small child. Additionally, the elongated members which are affixed to the hinges are shown loosely captured within flexible pockets and would be deficient in properly controlling the knee's movement in order to foster optimum healing. U.S. Pat. No. 4,136,404 discloses apparatus specifically intended to be connected to the sides of a ski boot. U.S. Pat. No. 4,220,148 discloses a stabilizer but does not disclose the cushion sheets, elongated braces and improved knee brace hinge with the plurality of elongated straps in accordance with this invention. U.S. Pat. No. 4,233,967 discloses a plastic contruction that does not have the sheets for selectively attaching the pairs of elongated braces and does not have the improved connecting hinge in accordance with this invention. U.S. Pat. No. 4,241,730 discloses a knee support which includes a pair of pivotally inter-connected rigid braces having one or more hinges; but does not include elongated braces, cushion sheets with improved hinge in accordance with this invention. Additionally, there are commercially available products such as "universal knee splints" or other knee immobilizers that have solved one or more special problems but none of them have offered the versatility that has often been desired by doctors and patients to foster healing and provide comfort and expressed hereinbefore. Hence the prior art has failed to supply the need for an improved knee brace incorporating a hinge that can allow simulated movement of a knee and restrain the patient's range of mobility selectively and adjustably while allowing and even facilitating removal for hygenic purposes or other reasons.

SUMMARY OF THE INVENTION

Accordingly, it is an object of this invention to provide external bracing apparatus having an improved knee brace hinge that will obviate the disadvantages of the prior art, is capable of being quickly and easily applied and which requires no messy compounds or uncomfortable curing.

It is a specific object of this invention to provide a brace that is lightweight, can be readily removed or adjusted in both its placement on the leg of the wearer as well as having the degree of mobility of the proximal and distal members changed; and still provide all of the original effectiveness and allows alleviating the problem of swelling and/or muscle atrophy.

It is a specific object of this invention to provide an economical, lightweight knee brace which has sufficient durability to be functional throughout the entire healing process of most typical knee injuries; but accomplishes the objects delineated above as well as other objects that will be apparent from reading of the descriptive matter hereinafter, particularly when taken in conjunction with the appended claims and drawings.

In accordance with one embodiment of this invention, there is provided an improvement in external bracing apparatus for controlling the degree of motion permitted by a wearer's knee, including:
a. first and second pairs of elongate braces, with each of the braces being relatively stiff so as to resist both torsion and bending loads, the first pair of elongate braces being adapted to lie on opposite sides of the wearer's thigh and the second pair of elongate braces being adapted to lie on opposite sides of the wearer's calf;
b. means for adjustably placing and holding respective pair of elongate braces in a desired attained position on respective opposite sides of the thigh and calf of the wearer with a hinge means positioned correctly adjacent the wearer's knee; and
c. an improved hinge means connected respectively with the central ends of the first and second pair of elongate braces.

In accordance with another embodiment of this invention, there is provided the improved hinge means, per se.

In any event, the improved hinge has a single cam-slot operator for simulating flexural motion of the wearer's knee and a positive lock for limiting the range of the flexural motion. The hinge means has a shaft contained in a mating aperture and slideably contained within a slot for allowing the flexural motion simulating that of the wearer's knee.

In a preferred embodiment, the hinge has a slot simulating a path of traverse of a spot in flexural movement of the wearer's knee and a cam means that follows the spot. This combination is incorporated in a first member and at least one second member that coengage each other and are adapted to move pivotally about the central shaft with respective aperture and slot combinations allowing the simulated motion of the knee. In a still more preferred embodiment, there are a pair of the second members that sandwich the first member in between; the slot penetrates completely through the first member; and the cam comprises a pin shaft that extends through the slot and engages each of the second members on both sides so as to positively restrict motion when movement of the cam is restricted by flexible plungers that are moveably disposed in the respective ends of the slot for restricting the range of movement of the cam and hence of the proximal and distal members with respect to each other. Also in the still more preferred embodiment of the invention, there are provided respective threaded apertures and engaging nuts with indicators and indices to facilitate pre-positioning of the respective flexible plungers to limit the range of motion as desired.

BRIEF DESCRIPTION OF THE DRAWINGS

FIG. 2c is an end view of the top of the hinge of FIG. 2a.

FIG. 3 is a partial cross-sectional view of the first member of the knee brace hinge of FIG. 2a.

DESCRIPTION OF PREFERRED EMBODIMENT(S)

It is to be borne in mind that this invention may be useful in other applications such as limiting the movement of the upper and lower arm members or the like; but it will be described herein as used in allowing healing of the leg injury such as a knee injury.

Figure 1:
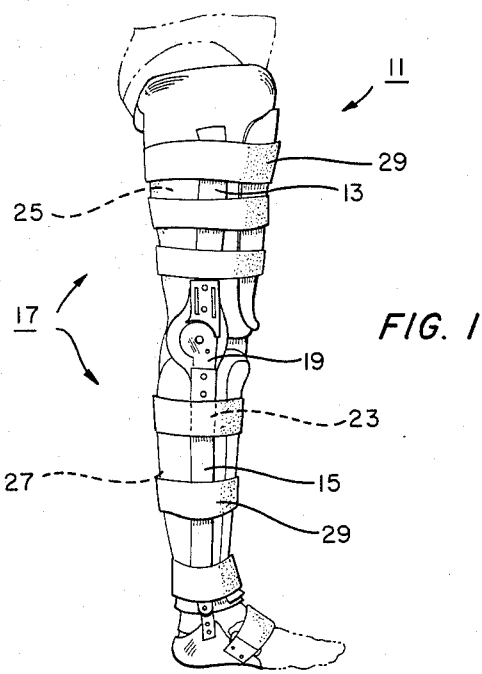
FIG. 1 is a side elevational view showing one embodiment of this invention.

Referring initially to FIG. 1, an external bracing apparatus 11 is illustrated for controlling the degree of motion which is permitted by a wearer's knee. The apparatus 11 includes first and second pairs of elongate braces 13, 15, means 17 for adjustably placing and holding the respective pairs of elongate braces in a desired attained position on respective opposite sides of the thigh and calf of the wearer with a hinge means 19 correctly positioned adjacent the wearer's knee.

Each of the braces is relatively stiff so as to resist both torsion and bending loads. A preferred structural material for the core of the braces is an elongate piece of aluminum having predetermined width and thickness; for example, about 2 centimeters wide and about 3 millimeters thick. The respective braces have their central ends 21, 23 connected with their respective hinge means 19. The braces are adapted to be positioned on opposite sides of the wearer's thigh and calf. As illustrated, the first pair of braces are adapted to be emplaced on respective sides of the wearer's thigh 25 and the second pair of braces are adapted to be emplaced along the respective sides of the wearer's calf 27.

Any other structurally strong bracing material can be employed. The type braces employed in the prior art may be employed herein and the respective braces, whether or not they employ a Velcro material for being held in place, will depend upon the type of means 17 for placing and holding the elongate braces in a desired attained position.

The means 17 for placing and holding the braces in a desired attained position may comprise any of those employed heretofore in the prior art. It is necessary that the means be adequate to hold the respective pairs of elongate braces in a desired attained position on respective opposite sides of the thigh and calf of the wearer with a hinge means correctly positioned adjacent the wearer's knee. A preferred embodiment is described and claimed in the aforementioned Ser. No. 227,381 "Brace For Articulated Limbs", filed Jan. 22, 1981. As described in that patent application, the means 17 may include a flexible sheet of cushion material which is adapted for being wrapped snugly around the wearer's thigh and around the wearer's calf. A preferred type of flexible material is the medium-density, open-cell polyurethane foam having a thickness of about three-eighths inch. This material is sufficiently porous to alleviate problems with sweating under normal conditions; is lightweight; and will not ordinarily cause an allergic skin reaction. The material is readily contourable to match a person's leg and is capable of being washed as required without losing its shape or structural integrity. Preferably, a length sufficient to encompass more than half of the length of the wearer's thigh and calf, respectively, will be employed in order to provide a substantial "anchor" that will ensure that there is essentially no movement of the knee—if that be the object to be achieved. A preferred length for the thigh piece of material is about 30 centimeters. Preferably, the top edge of the flexible sheet will be straight while the bottom will have a bell shaped recess in its center to preclude interference with the back of the leg or other part of the means 17. In a preferred embodiment, the outer surface of the flexible sheet has a polyester pile bonded thereto for engaging resilient hooks of the type commonly employed in the fasteners of the Velcro fastener. By using a bonded pile on the outside of the foam material, it is possible to employ only one size for the thigh and have it large enough to wrap circumferencially around essentially all adult legs. The soft material can be easily cut with scissors, however, such that it can be sized to fit a small child. There are no fasteners along the edge of the sheet so trimming away excess material poses no problem. Preferably the flexible sheet has a generally trapezoidal shape so as to foster a natural fit around a person's naturally tapered thigh. A typical sheet size for adults will have a top edge of about 70 centimeters and a bottom edge of about 55 centimeters.

Similarly, the flexible sheet adapted for fitting snugly around the wearer's calf will have a "universal size" that is about 40 centimeters long and has a width sufficient to envelope at least half of the calf of the wearer. An exemplary width is about 50 centimeters at the top and about 35-40 centimeters at the bottom.

Preferably the means 17 also includes a plurality of tabs of hook-type fastener material to position a respective piece around the wearer's legs. The tabs are made and located as described in the aforementioned Ser. No. 227,381 and may be relatively small to conserve material and minimize cost.

If desired, respective stays and stay pockets can be employed as described in the aforementioned Ser. No. 227,381, all as a part of the means 17 for holding the braces in place.

Preferably straps 29 will be employed as an essential part of retaining the respective braces in place. The straps 29 may be non-elastic or may be stretchable with a relatively high co-effecient of elasticity as long as they have the desired strength and lack of resiliency to hold the braces in place. Preferably, the straps have a breaking strength of over 400 pounds in order that there be no risk of failure which might be occasioned by an unusual flexing of the muscle or unexpected load caused by accidental fall or the like. The straps may be secured by respective D-rings at the ends and with respective pieces of Velcro resilient hook material to create the desired tension in holding the braces in place. If desired, the direction of pulling on the straps may be alternated in order to tighten them when installing the apparatus 11. The straps will be employed about both the thigh and calf region to hold the respective braces and, if employed, stays, so as to keep the knee brace hinge properly positioned.

The main thrust of this invention lies in the knee brace hinge 19. Ordinarily, a pair of respective hinge means 19 are disposed on both respective sides of the knee and are connected respectively with the respective first and second pairs of elongate braces at their respective central ends. The hinge means 19 has a single cam-slot operator for simulating flexural motion of the wearer's knee and a positive lock for limiting the range of flexural motion. The hinge means 19 has a shaft 31, FIG. 2a, contained in a mating aperture 33, FIG. 3, and slideably disposed within a slot 35, FIGS. 2a, 4 for allowing the flexural motion simulating that of the wearer's knee. Specifically, the shaft extends through the aperture 33 and the slot 35. The shaft 31 has a flange larger than the lateral dimensions of the respective slot and aperture on one end; and a washer having the same large diameter is then placed on the opposite side and riveted, or bradded in place. The shaft can be emplaced in any other satisfactory manner.

The hinge means are connected respectively with the respective centrals ends of the first and second elongate braces with a substantially inflexible connection. As illustrated, the central end 21 is inserted in a co-engaging well in the first end 39 of the hinge means 19 and riveted into position. To facilitate the riveting into place, holes are pre-drilled in the first end 39 and in the central end 21 of the first brace 13. The well is in between the respective indices, described later hereinafter. The second end 41 of the hinge means 19 has respective flanges 43 that engage the edge of the central end 23 of the second brace 15. Again, rivets are disposed through respective mating apertures to hold the brace 15 inflexibly connected with the second end 41 of the hinge 19.

Figure 2A:
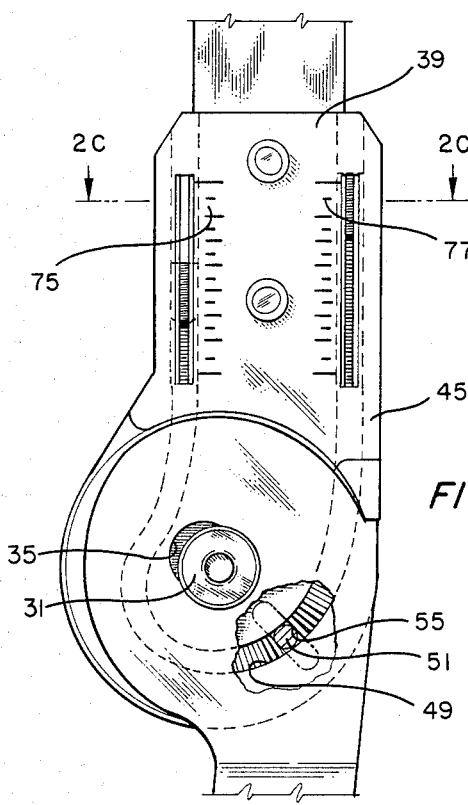
FIG. 2a is a side elevational view of the improved knee brace hinge of FIG. 1.
Figure 2B:
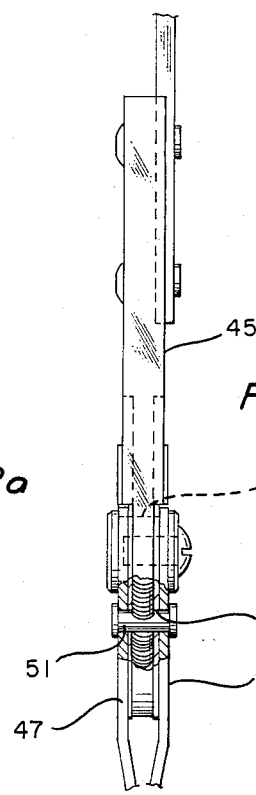
FIG. 2b is a cross-sectional view of the knee brace hinge of FIG. 2a showing the cam in its slot in accordance with a preferred embodiment thereof.
Figure 2C:
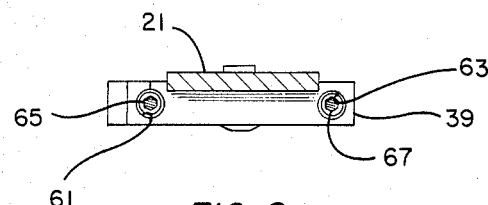

The hinge means 19 includes as its single cam-slot operator, a first member having a slot simulating a path of traverse of a spot in flexure of the wearer's knee and at least one second member having a cam means engaging the slot so as to traverse the slot in flexion, or flexural motion. The first member and at least one second member co-engage each other and are adapted to move pivotally with respect to each other about the central shaft 31 engaging the respective aperture 33 and slot 35. As illustrated and preferably, the hinge means 19 includes two second members 47 sandwiching therebetween the first member 45. FIG. 2b with a slot 49, FIGS. 2a,b and 3, extending completely through the first member 45. In the illustrated embodiment the cam comprises a pin shaft 51, FIGS. 2a, 2b, 3, 4. The pin shaft 51 is riveted and slideably engages slot 53 in washer 54 and engages positively respective apertures 55, FIGS. 2a, 4, in the second member 47. In this way the pins lock the cam to the second members such that restricting the movement of the cam in the slot 49 restricts movement of the second members 47 with respect to the first member 45. This, in turn, limits flexion and extension of the wearer's lower leg, or distal member.

Figure 3:
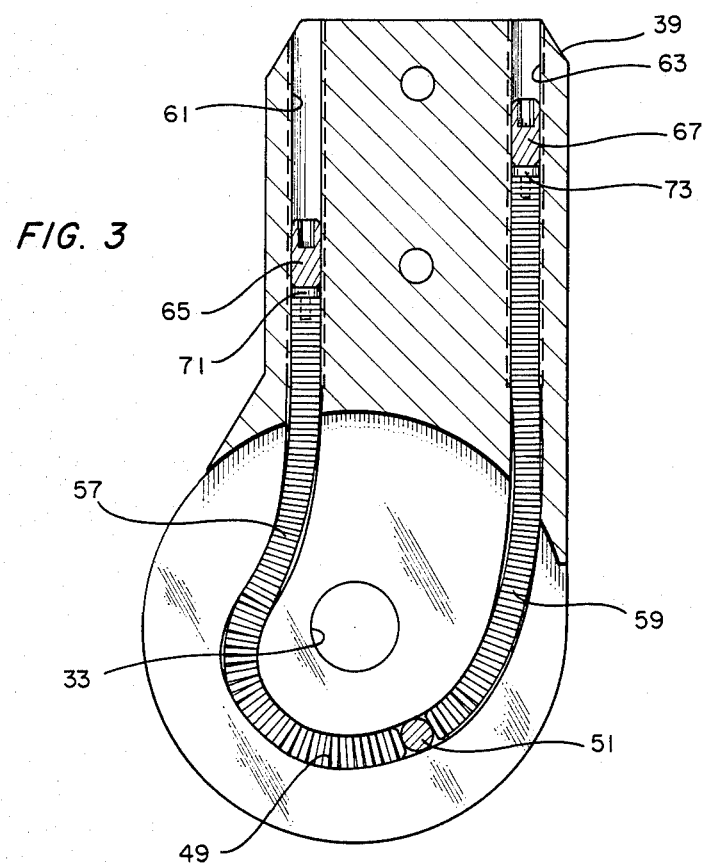

The positive lock for limiting the range of the flexion comprises flexible plunger means; such as, the springs 57, 59, FIG. 3; that are moveably disposed in respective ends of the slot for restricting the movement of the cam 51.

Figure 4:
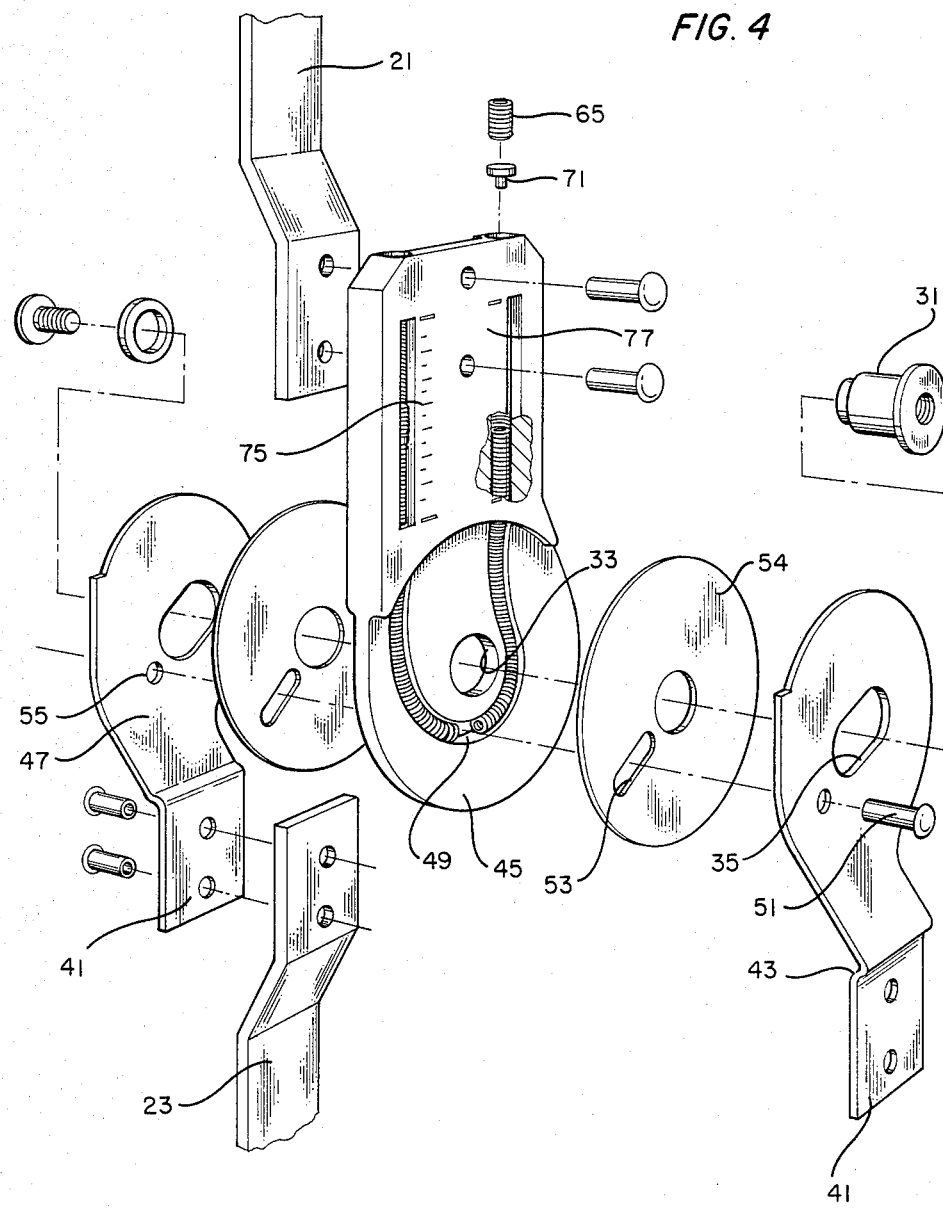
FIG. 4 is an exploded view of a hinge similar to that of FIG. 1.

In the illustrated embodiments, the slot 49 terminates in respective threaded bores 61, 63 at its respective ends and respective threaded nuts 65, 67, FIG. 3, are rotatably screwed into respective threaded bores for moving the flexible plungers 57, 59. Each of the nuts 65, 67 has an associated indicator 71, 73 that moves longitudinally of its threaded bore as the respective nut is moved longitudinally thereof. Indices 75, 77, FIGS. 2a, 4 are provided for indicating the degrees of a motion allowed in flexion and extension. As indicated, the degrees are shown ranging, inversely in the two, from 0 degrees to 140 degrees of motion. Preferably the respective indicators may be of anodized aluminum such as red anodized aluminum or the like. If desired, they can be rotatably affixed with the respective nuts 65, 67 or plungers. Ordinarily, this is unnecessary since they tend to follow and can be made to follow the nuts by flexure of the hinge means 19. The flexure causes the cam 51 to move the respective springs to maintain the indicators adjacent the respective nuts with which they are associated. This reduces the expense of a more elaborate and respective interconnections.

The respective members of the hinge and the nuts may be formed of any material. As illustrated, they are formed of aluminum to facilitate machining and the like. If desired, on the other hand, plastics such as Nylon, Delrin, or other machinable plastics; or even easily cleanable and relatively non-corrodable metal such as stainless steel can be employed. In fact, mild steel or other materials can be employed although special care must be taken to prevent corrosion or the like which can worsen the hygiene problem with such materials.

As can be seen in FIG. 2a, the first and second members 45, 47 have co-engaging recess and shoulder means 79 to serve as a positive stop to prevent hyper extension. As illustrated, the recess is on the second member 47 and the shoulder is on the first member 45, although this is relatively immaterial as long as a positive stop is provided.

In operation, the apparatus 11 is applied to patient's leg as described in the aforementioned U.S. Ser. No. 227,381. For example, an ankle cuff may be secured around the ankle if desired and the calf section positioned properly followed by positioning of the thigh section properly. The braces 13 and 15 are then optionally affixed in their respective positions, preferably after having been connected at their central ends with a respective hinge means 19. The hinge means 19 will be assembled by sandwiching the first piece 45 intermediate the two second pieces 47 with the shaft 31 inserted through the slots 35 and matingly engaging the aperture 33 in the first member 45. The washer is riveted into place on the shaft 31 so as to keep the members in place. The central ends 21, 23 of the respective braces are riveted into their respective places to form a rigid connection with the first and second ends 39, 41 of the hinge means 19. Thereafter, the remainder of the means 17 is secured in place with respective straps 29. Suitable Velcro strips or the like may be employed in connection with the respective braces to ensure that they are held in place with the knee brace hinge properly in place on both sides of the knee.

The hinge will have the desired degrees of flexion and extension set by screwing the nuts 65, 67 to properly position the adjacent indicators and plungers against movement of the cam 51 in the slot 49. As illustrated the screwing of the nuts is accomplished by an Allen wrench, although other means; such as, regular screw, Phillips head screw, torsion screw; can be employed if desired.

As noted hereinbefore, the respective means 17 can be removed at will, replaced with a new tighter fit if swelling should decrease and the apparatus 11 begins to feel loose. Unlike the previous types of permanent casts and the like, the apparatus 11 is easily and quickly adjustable, removed for hygiene or the like. Straps are easily tightened or removed, in fact, the entire installation will usually take five minutes or less.

Moreover, the weight of this semi-rigid apparatus will range from only 1 to 1.5 kilograms while most cast braces will usually weigh twice as much.

Thus it can be seen that this invention accomplishes the objects delineated hereinbefore.

Although this invention has been described with a certain degree of particularity, it is understood that the present disclosure is made only by way of example and that numerous changes in the details of construction and the combination and arrangement of parts may be resorted to without departing from the spirit and the scope of the invention, reference being had for the latter purpose to the appended claims.

What is claimed is:

1. An external bracing apparatus for controlling the degree of motion permitted by a wearer's knee, including:
   a. first and second pairs of elongate braces, with each of said braces being relatively stiff so as to resist both torsion and bending forces; said first pair of elongate braces being adapted to lie on opposite sides of the wearer's thigh and said second pair of elongate braces being adapted to lie on opposite sides of the wearer's calf;
   b. means for adjustably placing and holding said respective pairs of elongate braces in desired attained positions on respective opposite sides of said thigh and calf of said wearer with a hinge means positioned correctly adjacent the wearer's knee;
   the improvement comprising:
   c. a pair of respective hinge means connected respectively with said first and second pairs of elongate braces at their respective central ends; each said hinge means having a single cam-slot operator for simulating flexural motion of the wearer's knee, and a positive lock for limiting the range of said flexural motion; said hinge means having a shaft contained in a mating aperture and slideably contained within a slot for allowing flexural motion simulating the motion of the wearer's knee.

2. The bracing apparatus of claim 1 wherein said hinge means are respectively connected with respective said first and second elongate braces with a substantially inflexible connection.

3. The bracing apparatus of claim 2 wherein substantially inflexible connection comprises a plurality of rivets penetrating laterally through respective said braces and ends of said hinge means.

4. The bracing apparatus of claim 3 wherein each said hinge means includes at one end a well for receiving a central end of a said brace and includes at a second end flanges at respective edges for receiving a central end of a said brace and said ends of said hinge means and said braces have co-engaging apertures for receiving said rivets; said central ends of said first pair of braces are received within respective wells in said one end of respective said hinge means and riveted in place; and said central ends of said second pair of braces are received between bent over flanges of said second end and are riveted in place.

5. The bracing apparatus of claim 1 wherein said hinge means includes a first member having a slot simulating a path of traverse of a spot in flexural movement of the wearer's knee and at least one second member having a cam means engaging said slot so as to traverse said slot in flexural motion; said first and at least one second member co-engaging each other and adapted to move pivotally with respect each other with said central shaft engaging said aperture and said slot for allowing said flexural motion simulating that of the wearer's knee.

6. The bracing apparatus of claim 5 wherein each said hinge means includes two said second members sandwiching said first member therebetween; said slot extends completely through said first member; said cam is laterally disposed within said slot and extends laterally to engage positively both said second members such that the restraint of motion of said cam restricts motion of said ends of said hinge means and hence restrains motion of said braces and the wearer's calf with respect to the wearer's thigh.

7. The bracing apparatus of claim 6 wherein said positive lock comprises respective flexible plunger means that are moveably disposed in the respective ends of said slot for restraining the range of movement of said cam.

8. The bracing apparatus of claim 7 wherein each end of each said slot terminates in a threaded bore and respective threaded nuts are rotatably screwed into respective threaded bores for moving said flexible plungers.

9. The bracing apparatus of claim 8 wherein each said threaded nut has an associated indicator that moves longitudinally of its respective threaded bore as its associated said nut is moved and respective indices are provided for indicating the degrees of flexural motion permitted by said nuts and plungers; said indices indicating degrees of flexion and degrees of extension permitted.

10. The bracing apparatus of claim 5 wherein said first and second members have co-engaging recess and shoulder means for preventing hyperextension of the wearer's leg.

11. A knee brace hinge comprising:
a. a first member and at least one second member having a single, co-acting cam-slot operator for simulating flexural motion of a wearer's knee; having a positive lock for limiting the range of flexural motion;
b. a central shaft, aperture and slot combination for effecting relative pivotal motion between respective said first and second members in the form of simulated pivotal movement of the wearer's knee; and
c. means for connecting with respective elongate braces for emplacing on respective sides of a leg of a wearer with said hinge properly located adjacent the wearer's knee.

12. The knee brace hinge of claim 11 wherein said hinge means includes a first member having a slot simulating a path of traverse of a spot in flexural movement of the wearer's knee and at least one second member having a cam means engaging said slot so as to traverse said slot in the flexural motion; said first and at least one second member co-engaging each other and adapted to move pivotally with said central shaft engaging said aperture and slot so as to allow said flexural motion.

13. The knee brace hinge of claim 12 wherein said hinge includes two said second members sandwiching said first member therebetween; said slot extends completely through said first member; said cam is slideably disposed in said slot and extends laterally to engage positively both said second members such that the restraint of motion of said cam restricts motion of said ends of said hinge means and hence restricts motion of said braces and the wearer's calf with respect to wearer's thigh.

14. The knee brace hinge of claim 13 wherein said positive lock comprises respective flexible plunger means that are moveably disposed in respective ends of said slots for restricting the range of movement of said cam.

15. The knee brace hinge of claim 14 wherein each end of each said slot terminates in a threaded bore and respective threaded nuts are rotatably screwed into respective said threaded bores for moving said flexible plungers.

16. The knee brace hinge of claim 15 wherein each said nut has an associated indicator that moves longitudinally of its respective threaded bore as its associated said nut is moved and respective indices are provided for indicating the degrees of flexural motion permitted by said nuts and plungers; said indices indicating degrees of movement in flexion and extension respectively permitted.

17. The knee brace hinge of claim 11 wherein said first and second members have co-engaging recess and shoulder means for preventing hyperextension of a wearer's leg.

* * * * *